US011458135B2

(12) United States Patent
Nirogi et al.

(10) Patent No.: US 11,458,135 B2
(45) Date of Patent: *Oct. 4, 2022

(54) COMBINATION OF PURE 5-HT6 RECEPTOR ANTAGONISTS WITH ACETYLCHOLINESTERASE INHIBITORS

(71) Applicant: SUVEN LIFE SCIENCES LIMITED, Telangana (IN)

(72) Inventors: Ramakrishna Nirogi, Telangana (IN); Anil Karbhari Shinde, Telangana (IN); Pradeep Jayarajan, Telangana (IN); Gopinadh Bhyrapuneni, Telangana (IN); Ramasastri Kambhampati, Telangana (IN); Venkateswarlu Jasti, Telangana (IN)

(73) Assignee: Suven Life Sciences Limited, Hyderabad (IN)

( * ) Notice: Subject to any disclaimer, the term of this patent is extended or adjusted under 35 U.S.C. 154(b) by 604 days.

This patent is subject to a terminal disclaimer.

(21) Appl. No.: 16/099,161

(22) PCT Filed: Aug. 3, 2016

(86) PCT No.: PCT/IB2016/054673
§ 371 (c)(1),
(2) Date: Nov. 5, 2018

(87) PCT Pub. No.: WO2017/199071
PCT Pub. Date: Nov. 23, 2017

(65) Prior Publication Data
US 2019/0125743 A1 May 2, 2019

(30) Foreign Application Priority Data
May 18, 2016 (IN) .............................. 201641017205

(51) Int. Cl.
*A61K 31/496* (2006.01)
*A61P 25/28* (2006.01)
*A61K 31/445* (2006.01)
*A61K 31/31* (2006.01)
*A61P 25/18* (2006.01)
*A61P 25/16* (2006.01)

(52) U.S. Cl.
CPC ............ *A61K 31/496* (2013.01); *A61K 31/31* (2013.01); *A61K 31/445* (2013.01); *A61P 25/28* (2018.01); *A61P 25/16* (2018.01); *A61P 25/18* (2018.01)

(58) Field of Classification Search
CPC .... A61K 31/496; A61K 31/31; A61K 31/445; A61K 2300/00; A61K 31/27; A61P 25/28; A61P 25/18; A61P 25/16
See application file for complete search history.

(56) References Cited

U.S. PATENT DOCUMENTS

2007/0167431 A1    7/2007  Comery
2010/0120747 A1 *  5/2010  Codony-Soler ......... A61P 25/02
                                                    514/217.01

FOREIGN PATENT DOCUMENTS

| WO | 2004/048330 | 6/2004 | |
| WO | WO-2004048330 A1 * | 6/2004 | ............. A61P 25/30 |
| WO | 2007/087151 | 8/2007 | |
| WO | 2007/147883 | 12/2007 | |
| WO | 2008/002539 | 1/2008 | |
| WO | 2014/037532 | 3/2014 | |
| WO | 2015/083179 | 6/2015 | |

OTHER PUBLICATIONS

Bhyrapuneni et al., The 5-HT6 Antagonist SUVN-502 Potentiates the Effects of Acetylcholinesterase Inhibitors on Extracellular Acetylcholine Levels and in Animal Models of Cognition, Alzheimer's & Dementia, vol. 11, Issue 7S_Part_10, pp. P456-P500, Jul. 2015 (Year: 2015).*
Donepezil prescribing information (Year: 2012).*
Ramakrishna Nirogi, Development and validation of sensitive LC-MS/MS method for thequantification of SUVN-502 and its metabolite and its application forfirst in human pharmacokinetic study, Journal of Pharmaceutical and Biomedical Analysis 145 (2017) 423-430 (Year: 2017).*
Ramakrishna Nirogi et al., P3-451: SUVN-502: A potent and selective 5-HT6 antagonist, potential drug for thetreatment of Alzheimer's disease, Alzheimer's & Dementia / vol. 7, Issue 4S_Part_19 / p. S659-S659, First published: Jul. 1, 2011, https://doi.org/10.1016/j.jalz.2011.05.1895 (Year: 2011).*
PubChem entry for masupirdine ; create Oct. 25, 2006 (Year: 2006).*
Tse et al., "Disposition and metabolic profiling of [(14)C] cerlapirdine using accelerator mass spectrometry" Drug Metabolism and Disposition 42:2023-2032 (Dec. 2014).
"Response to Written Opinion" submitted to the European Patent Office in PCT Application No. PCT/IB2016/054673 and dated May 8, 2017.
Wicke et al., "Investigational drugs targeting 5-HT6 receptors for the treatment of Alzheimer's disease" Exp. Op. Invest. Drugs 24(12):1515-1528 (2015).
European Patent Office, "International Search Report" and "Written Opinion" dated Feb. 1, 2017 in PCT Application No. PCT/IB2016/054673.
European Patent Office, "International Preliminary Report on Patentability" completed Apr. 17, 2018 in PCT Application No. PCT/IB2016/054673.
Thompson et al., "The benefits and risks associated with cholinesterase inhibitor therapy in Alzheimer's disease", Exp. Op. on Drug Safety 3:425-440 (2004).

(Continued)

Primary Examiner — Kortney L. Klinkel
Assistant Examiner — Jason Deck
(74) Attorney, Agent, or Firm — IpHorgan Ltd.

(57) ABSTRACT

The present invention relates to pure 5-HT6 receptor antagonists, or the pharmaceutically acceptable salt(s) thereof in combination with or as adjunct to acetylcholinesterase inhibitors and their use in the treatment of cognitive disorders. The invention further provides the pharmaceutical composition containing the said combination.

38 Claims, 6 Drawing Sheets

(56) References Cited

OTHER PUBLICATIONS

Birks JS, "Cholinesterase inhibitors for Alzheimer's disease (Review)" Cochrane Database Systematic Reviews (2006) Issue 1, Article No. CD005593, pp. 1-102.
Monsma et al., "Cloning and Expression of a Novel Serotonin Receptor with High Affinity for Tricyclic Psychotropic Drugs" Molec. Pharmacol. 43:320-327 (1993).
Bentley et al., "Investigation of stretching behaviour induced by the selective 5-HT6 receptor antagonist, Ro 04-6790, in rats" Br. J. Pharmacol. 126:1537-42 (1999).
Woolley et al., "5-ht6 Receptors" CNS & Neurol. Disorders—Drug Targets 3:59-79 (2004).
Kohen et al., "Cloning of the mouse 5-HT6 serotonin receptor and mutagenesis studies of the third cytoplasmic loop" Molec. Brain Res. 90:110-117 (2001).
Romero et al., "Efficacy of selective 5-HT6 receptor ligands determined by monitoring 5-HT6 receptor-mediated cAMP signaling pathways" Br. J. Pharmacol 148:1133-1143 (2006).

\* cited by examiner

Data represents Mean ± SEM of Exploration Time

**p<0.01 Vs familiar object (Paired 't' test). N=6-33

Data represents Mean ± SEM of Exploration Time

*p<0.05 Vs familiar object (Students paired 't' test). N=8-11

Data represents Mean ± SEM of Exploration Time

*p<0.05 Vs familiar object (Students paired 't' test). N=8-10

(a)

(b)

(a) Values are expressed as mean ± S.E.M. $p$ <0.01, *$p$ <0.001 (Bonferroni post test) (b) Cumulative increases in neurotransmitter above baseline expressed as a percentage of the area under the curve ± S.E.M. **$p$ <0.01 (Dunnett's Multiple Comparison Test).

(a)

(b)

(a) Data expressed as Mean ± S.E.M. *$p<0.05$, $p<0.01$, *$p<0.001$ Vs Donepezil alone (Bonferroni posttest) (b) Cumulative increases in neurotransmitter above baseline expressed as a percentage of the area under the curve ± S.E.M. **$p<0.01$ Vs Donepezil alone (Dunnett's Multiple Comparison Test)

(a)

(b)

(a) Data expressed as Mean ± S.E.M. *$p<0.001$ Vs Rivastigmine alone (Bonferroni posttest) (b) Cumulative increases in neurotransmitter above baseline expressed as a percentage of the area under the curve ± S.E.M. $p<0.01$ Vs Rivastigmine alone (Dunnett's Multiple Comparison Test)

Data expressed as Mean ± S.E.M. **$p<0.01$ Vs Donepezil alone (Bonferroni posttest)

COMBINATION OF PURE 5-HT6 RECEPTOR ANTAGONISTS WITH ACETYLCHOLINESTERASE INHIBITORS

CROSS REFERENCE TO RELATED APPLICATIONS

This application is a national stage completion application of PCT Application No. PCT/IB2016/054673, filed Aug. 3, 2016, and claims the benefit of India Application No. 201641017205, filed May 18, 2016. Each of these applications is incorporated by reference herein in its entirety.

FIELD OF THE INVENTION

The present invention relates to pure 5-HT$_6$ receptor (5-HT$_6$R) antagonists, or the pharmaceutically acceptable salt(s) thereof in combination with or as adjunct to acetylcholinesterase inhibitors and their use in the treatment of cognitive disorders. The invention further relates to the pharmaceutical composition containing the said combination.

BACKGROUND OF INVENTION

Alzheimer's disease (AD) is the most common cause of dementia worldwide. The exponential rise in the number of cases of AD in the past and the future projection over the next few decades is anticipated to result in great pressure on the social and health-care systems of developed and developing economies alike. AD also imposes tremendous emotional and financial burden to the patient's family and community.

The current list of approved cognitive enhancing drugs for AD is not long and historically been focused on acetylcholinesterase inhibitors (donepezil, galantamine and rivastigmine). These drugs act by inhibiting the hydrolysis of acetylcholine (ACh) into acetate and choline by targeting acetylcholinesterase (AChE) enzyme. Increasing the ACh levels in the synapse can stimulate cholinergic receptors and promote memory function. Although acetylcholinesterase inhibitors (AChEIs) can temporarily delay the progression of cognitive decline in AD, the effects are modest. ACh being present both in the central and peripheral nervous system, AChEIs produce several undesirable side effects such as gastrointestinal disturbances, bradycardia and excessive salivation that are associated with an action on peripheral muscarinic cholinergic receptors (*Expert Opinion on Drug Safety*, 3, 2004, 425-440). The limitation of acetylcholinesterase inhibitor class of drugs is that they are poorly tolerated, their efficacy is not sustained and they require constant dose-titration as the disease progresses (*Cochrane Database Systematic Reviews*, 2006, CD005593) which lead to significant patient noncompliance. The incidence and the severity of these side effects increase with the dose and in general are more pronounced at the initiation of the treatment or after dose increase. Hence there is an unmet need of alternate therapy for treating cognition disorders.

5-Hydroxytryptamine 6 receptor (5-HT$_6$R) is a member of GPCR family and is exclusively expressed in the brain, particularly in areas associated with cognition, such as hippocampus and frontal cortex (*Molecular Pharmacology*, 1993, 43, 320-327). Activation of 5-HT$_6$R usually represses cholinergic function (*British Journal of Pharmacology*, 1999, 126, 1537-1542), whereas blockade of the receptor improves the cognitive functions. Thus, 5-HT$_6$R may be a viable target for pharmacologic intervention to improve the cognitive function of patients with AD. As 5-HT$_6$R is exclusively located centrally, it is believed that 5-HT$_6$R antagonists would have limited peripheral side effects, including the ones which are commonly associated with cholinesterase inhibitors. Antagonism of this receptor by several investigational compounds has been shown to improve learning and memory in animal models (*CNS & Neurological Disorders—Drug Targets*, 2004, 3, 59-79).

Since blocking 5-HT$_6$R modulates cholinergic activity, one might expect 5-HT$_6$R antagonists to complement and/or augment cognitive function through this therapeutic mechanism. This may in turn help to reduce the side effects with better patient compliance and thus can be administered over a long period.

The compounds of the present invention are pure 5-HT$_6$R antagonists with high affinity and very high selectivity over closely related serotonin receptor subtypes and improves learning and memory in animals. This data support the hypothesis that use of the said compounds in combination with acetylcholinesterase inhibitors might enhance the cognitive function of patients with cognitive disorders. The 5-HT$_6$R antagonist compounds mentioned here are described in U.S. Pat. No. 7,875,605 which is incorporated by reference. The preparation of these compounds is given in the said patent.

In the applications, WO2014037532A1, WO2008002539A1, WO2007147883A1 and WO2007087151A2 combination of acetylcholinesterase inhibitors with 5-HT$_6$R antagonists are mentioned as useful option in the treatment of AD.

As the treatment of AD is chronic in nature, there is a desperate unmet medical need for better and safer treatment options. A therapeutic strategy eagerly sought for AD patients is to target an improvement with an adjunct to existing therapies that would bring additional relief for patients, lower the burden on the caregiver and allow the patient to enjoy a better quality of life without the need for institutional care and/or hospitalization.

The instant invention provides pure 5-HT$_6$R antagonists or the pharmaceutically acceptable salt(s) thereof, which may enhance the cognitive function of patients on treatment with acetylcholinesterase inhibitors. The present invention is based on the finding that the instant compounds with pure 5-HT$_6$R affinity enhances and also prolongs the effect of the acetylcholinesterase inhibitors. The combination of the instant invention demonstrates a synergistic effect in their pharmacological activity. Such combined administration of pure 5-HT$_6$R antagonist and acetylcholinesterase inhibitor can result in beneficial effect to improve the therapeutic efficacy in humans.

SUMMARY OF THE INVENTION

The object of the present invention is to provide an improved combination therapy for the treatment of cognitive disorders, such as Alzheimer's disease, schizophrenia, Parkinson's disease, lewy body dementia, vascular dementia or frontotemporal dementia.

In the first aspect, the present invention relates to combination of pure 5-HT$_6$ receptor antagonist and acetylcholinesterase inhibitor; wherein the pure 5-HT$_6$R antagonist is selected from:

1-[(2-Bromophenyl)sulfonyl]-5-methoxy-3-[(4-methyl-1-piperazinyl)methyl]-1H-indole;
1-[(4-Fluorophenyl)sulfonyl]-5-methoxy-3-[(4-methyl-1-piperazinyl)methyl]-1H-indole; and 1-[(4-Isopropylphenyl)sulfonyl]-5-methoxy-3-[(4-methyl-1-piperazinyl)methyl]-1H-indole; or a pharmaceutically acceptable salt thereof.

In another aspect, the present invention relates to combination of pure $5\text{-}HT_6$ receptor antagonist and acetylcholinesterase inhibitor; wherein the pure $5\text{-}HT_6$ receptor antagonist is 1-[(2-Bromophenyl)sulfonyl]-5-methoxy-3-[(4-methyl-1-piperazinyl)methyl]-1H-indole or a pharmaceutically acceptable salt.

In another aspect, the present invention relates to combination of pure $5\text{-}HT_6$ receptor antagonist and acetylcholinesterase inhibitor; wherein the pure $5\text{-}HT_6$ receptor antagonist is 1-[(4-Fluorophenyl)sulfonyl]-5-methoxy-3-[(4-methyl-1-piperazinyl)methyl]-1H-indole or a pharmaceutically acceptable salt thereof.

In another aspect, the present invention relates to combination of pure $5\text{-}HT_6$ receptor antagonist and acetylcholinesterase inhibitor; wherein the pure $5\text{-}HT_6$ receptor antagonist is 1-[(4-Isopropylphenyl)sulfonyl]-5-methoxy-3-[(4-methyl-1-piperazinyl)methyl]-1H-indole or a pharmaceutically acceptable salt thereof.

In another aspect, the present invention relates to combination of pure $5\text{-}HT_6$ receptor antagonist and acetylcholinesterase inhibitor; wherein the acetylcholinesterase inhibitor is selected from donepezil, galantamine and rivastigmine or a pharmaceutically acceptable salt thereof.

In another aspect, the present invention relates to combination of pure $5\text{-}HT_6$ receptor antagonist and acetylcholinesterase inhibitor; wherein the pure $5\text{-}HT_6$ receptor antagonist is 1-[(2-Bromophenyl)sulfonyl]-5-methoxy-3-[(4-methyl-1-piperazinyl)methyl]-1H-indole dimesylate monohydrate.

In yet another aspect, the present invention relates to combination of 1-[(2-Bromophenyl)sulfonyl]-5-methoxy-3-[(4-methyl-1-piperazinyl)methyl]-1H-indole or a pharmaceutically acceptable salt thereof with donepezil or a pharmaceutically acceptable salt thereof.

In yet another aspect, the present invention relates to combination of 1-[(2-Bromophenyl)sulfonyl]-5-methoxy-3-[(4-methyl-1-piperazinyl)methyl]-1H-indole or a pharmaceutically acceptable salt thereof with rivastigmine or a pharmaceutically acceptable salt thereof.

In yet another aspect, the present invention relates to combination of 1-[(2-Bromophenyl)sulfonyl]-5-methoxy-3-[(4-methyl-1-piperazinyl)methyl]-1H-indole or a pharmaceutically acceptable salt thereof with galantamine or a pharmaceutically acceptable salt thereof.

In yet another aspect, the present invention relates to the said combination for use in the treatment of cognitive disorders such as Alzheimer's disease, schizophrenia, Parkinson's disease, lewy body dementia, vascular dementia or frontotemporal dementia.

In yet another aspect, the present invention relates to method of treatment of cognitive disorders such as Alzheimer's disease, schizophrenia, Parkinson's disease, lewy body dementia, vascular dementia or frontotemporal dementia comprising administering to a patient in need thereof a therapeutically effective amount of the said combination.

In yet another aspect, the present invention relates to 1-[(2-Bromophenyl)sulfonyl]-5-methoxy-3-[(4-methyl-1-piperazinyl)methyl]-1H-indole or a pharmaceutically acceptable salt thereof for use in the adjunct treatment of cognitive disorders such as Alzheimer's disease, schizophrenia, Parkinson's disease, lewy body dementia, vascular dementia or frontotemporal dementia in a patient on treatment with a acetylcholinesterase inhibitor.

In yet another aspect, the present invention relates to 1-[(2-Bromophenyl)sulfonyl]-5-methoxy-3-[(4-methyl-1-piperazinyl)methyl]-1H-indole or a pharmaceutically acceptable salt thereof for use in combination with or adjunct to acetylcholinesterase inhibitor for the treatment of cognitive disorders such as Alzheimer's disease, schizophrenia, Parkinson's disease, lewy body dementia, vascular dementia or frontotemporal dementia.

In another aspect, the present invention relates to method for treatment of cognitive disorders comprising administering to a patient in need thereof a therapeutically effective amount of 1-[(2-Bromophenyl)sulfonyl]-5-methoxy-3-[(4-methyl-1-piperazinyl)methyl]-1H-indole or a pharmaceutically acceptable salt thereof in combination with or as an adjunct to donepezil or a pharmaceutically acceptable salt thereof.

In yet another aspect, the present invention relates to use of a combination of 1-[(2-Bromophenyl)sulfonyl]-5-methoxy-3-[(4-methyl-1-piperazinyl)methyl]-1H-indole or a pharmaceutically acceptable salt thereof and donepezil or pharmaceutically acceptable salts thereof for the treatment of cognitive disorders such as Alzheimer's disease, schizophrenia, Parkinson's disease, lewy body dementia, vascular dementia or frontotemporal dementia.

In another aspect, the present invention relates to pharmaceutical composition comprising $5\text{-}HT_6$ receptor antagonist in combination with acetylcholinesterase inhibitor and pharmaceutically acceptable excipients or combination thereof; wherein the $5\text{-}HT_6$ receptor antagonist is 1-[(2-Bromophenyl)sulfonyl]-5-methoxy-3-[(4-methyl-1-piperazinyl)methyl]-1H-indole or a pharmaceutically acceptable salt thereof and the acetylcholinesterase inhibitor is donepezil or a pharmaceutically acceptable salt thereof.

In another aspect, the present invention relates to pharmaceutical composition comprising 1-[(2-Bromophenyl)sulfonyl]-5-methoxy-3-[(4-methyl-1-piperazinyl)methyl]-1H-indole or a pharmaceutically acceptable salt thereof with donepezil or a pharmaceutically acceptable salt thereof and pharmaceutically acceptable excipients or combination thereof for use in the treatment of cognitive disorder such as Alzheimer's disease, schizophrenia Parkinson's disease, lewy body dementia, vascular dementia or frontotemporal dementia.

BRIEF DESCRIPTION OF THE DIAGRAMS

FIG. 1a depicts the results of the effect of co-treatment of compound 1 or compound 2 or compound 3 and donepezil on cognition enhancing properties using object recognition task model.

DETAILED DESCRIPTION

Figure 1A:
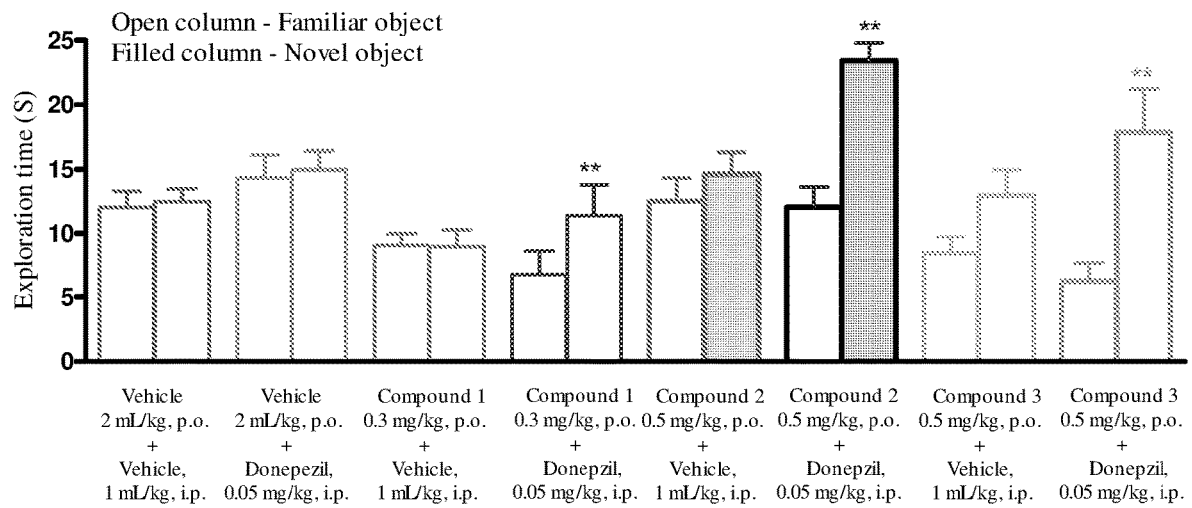
FIG. 1b depicts the results of the effect of a co-treatment of compound 1 and rivastigmine on cognition enhancing properties using object recognition task model.
FIG. 1c depicts the results of the effect of a co-treatment of compound 1 and galantamine on cognition enhancing properties using object recognition task model.

Unless otherwise stated, the following terms used in the specification and claims have the meanings given below:

The term, "5-HT$_6$ receptor antagonist" as used herein refers to a ligand or drug that has affinity towards 5-HT$_6$ receptor, blocks or inhibits the function/binding of agonist at the 5-HT$_6$ receptor.

The term, "pure 5-HT$_6$ receptor antagonist" as used herein refers to 5-HT$_6$ receptor antagonist which has very high selectivity (>250 fold) over the closely related serotonin subtypes like 5-HT$_{1A}$, 5-HT$_{1B}$, 5-HT$_{1D}$, 5-HT$_{2A}$, 5-HT$_{2C}$, 5-HT$_4$, 5-HT$_{5A}$ and 5-HT$_7$.

Examples of the pure 5-HT$_6$ receptor antagonists include,
1-[(2-Bromophenyl)sulfonyl]-5-methoxy-3-[(4-methyl-1-piperazinyl)methyl]-1H-indole;
1-[(4-Fluorophenyl)sulfonyl]-5-methoxy-3-[(4-methyl-1-piperazinyl)methyl]-1H-indole; and
1-[(4-Isopropylphenyl)sulfonyl]-methoxy-3-[(4-methyl-1-piperazinyl)methyl]-1H-indole;
or a pharmaceutically acceptable salt thereof.

Examples of pharmaceutically acceptable salt of the above identified compounds include but not limited to,
1-[(2-Bromophenyl)sulfonyl]-5-methoxy-3-[(4-methyl-1-piperazinyl)methyl]-1H-indole dimesylate monohydrate;
1-[(4-Fluorophenyl)sulfonyl]-5-methoxy-3-[(4-methyl-1-piperazinyl)methyl]-1H-indole dihydrochloride; and
1-[(4-Isopropylphenyl)sulfonyl]-methoxy-3-[(4-methyl-1-piperazinyl)methyl]-1H-indole dihydrochloride.

The term, "acetylcholinesterase inhibitor" as used herein is a chemical or drug that inhibits the acetylcholinesterase enzyme from breaking down to acetylcholine, thereby increasing both the level and duration of action of the neurotransmitter acetylcholine. Examples of acetylcholinesterase inhibitors are donepezil, galantamine and rivastigmine. Preferably, the acetylcholinesterase inhibitor is donepezil and rivastigmine. More preferably the acetylcholinesterase inhibitor is donepezil.

Donepezil is a drug approved for treatment of mild, moderate and severe dementia of Alzheimer's disease. Donepezil is a reversible inhibitor of the enzyme acetylcholinesterase and sold under trade name Aricept® as hydrochloride salt.

Rivastigmine is a drug approved for treatment of mild, moderate and severe dementia of Alzheimer's disease. Rivastigmine is a reversible cholinesterase inhibitor and sold under trade name Exelon® and Exelon Patch® as tartrate salt.

Galantamine is a drug approved for treatment of mild, moderate and severe dementia of Alzheimer's disease. Galantamine, a reversible, competitive acetylcholinesterase inhibitor and sold under trade name Razadyne® as hydrobromide salt.

The phrase, "therapeutically effective amount" is defined as an amount of a compound of the present invention that (i) treats the particular disease, condition or disorder, (ii) eliminates one or more symptoms of the particular disease, condition or disorder and (iii) delays the onset of one or more symptoms of the particular disease, condition or disorder described herein.

The term, "pharmaceutically acceptable salt" as used herein refers to salts of the active compound and are prepared by reaction with the appropriate acid or acid derivative, depending on the particular substituents found on the compounds described herein.

The term, "patient" as used herein refers to an animal. Preferably the term "patient" refers to mammal. The term mammal includes animals such as mice, rats, dogs, rabbits, pigs, monkeys, horses and human. More preferably the patient is human.

The term, "Alzheimer's disease" as used herein refers to a dementia that causes problems with memory, thinking and behavior. The Alzheimer's disease can be mild to severe.

The compound 1 as used herein is 1-[(2-Bromophenyl)sulfonyl]-5-methoxy-3-[(4-methyl-1-piperazinyl)methyl]-1H-indole dimesylate monohydrate which has the chemical structure,

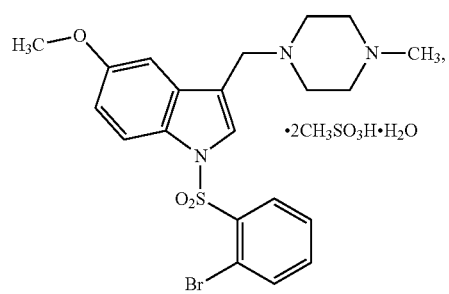

and the process for preparing this compound in large scale is described in WO2015083179A1.

The compound 2 as used herein is 1-[(4-Fluorophenyl)sulfonyl]-5-methoxy-3-[(4-methyl-1-piperazinyl)methyl]-1H-indole dihydrochloride which has the chemical structure,

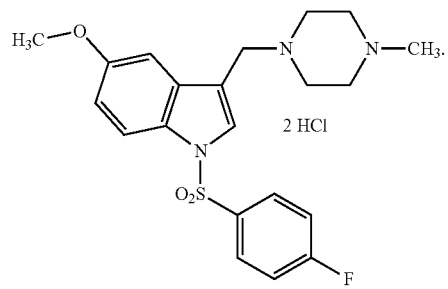 [SMILES: COc1ccc2c(c1)c(CN1CCN(C)CC1)cn2S(=O)(=O)c1ccc(F)cc1 ; "2 HCl"]

The compound 3 as used herein is 1-[(4-Isopropylphenyl)sulfonyl]-5-methoxy-3-[(4-methyl-1-piperazinyl)methyl]-1H-indole dihydrochloride which has the chemical structure,

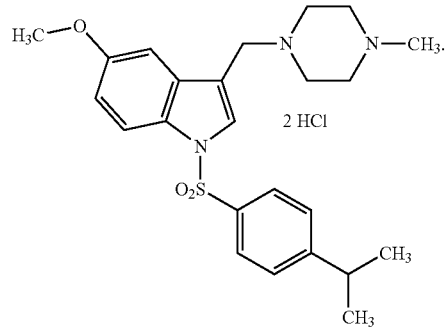 [SMILES: COc1ccc2c(c1)c(CN1CCN(C)CC1)cn2S(=O)(=O)c1ccc(C(C)C)cc1 ; "2 HCl"]

The term, "treatment' or 'treating" as used herein refers to any treatment of a disease in a mammal, including: (a) slowing or arresting the development of clinical symptoms; and/or (b) causing the regression of clinical symptoms.

The term, "compound for use" as used herein embrace any one or more of the following: (1) use of a compound, (2) method of use of a compound, (3) use in the treatment of, (4) the use for the manufacture of pharmaceutical composition/medicament for treatment/treating or (5) method of treatment/treating/preventing/reducing/inhibiting comprising administering an effective amount of the active compound to a subject in need thereof.

The term, "cognitive disorder" as used herein refers to a group of mental health disorders that principally affect learning, memory, perception and problem solving and include amnesia, dementia, and delirium. Cognitive disorders can result due to disease, disorder, ailment or toxicity. Example of cognitive disorders includes but not limited to, Alzheimer's disease, schizophrenia, Parkinson's disease, lewy body dementia (LBD), vascular dementia and frontotemporal dementia (FTD). Preferably the cognitive disorder is Alzheimer's disease.

The term, "adjunct" or "adjunctive treatment" as used herein refers to an additional treatment to a patient who has already received at least one other therapy for cognitive disorder. A drug used as adjunctive therapy is administered to a patient to make that primary treatment works better.

EMBODIMENTS

The present invention encompasses all the combinations described herein without limitation, however, preferred aspects and elements of the invention are discussed herein in the form of the following embodiments.

In one embodiment, the present invention provides a combination of 1-[(2-Bromophenyl)sulfonyl]-5-methoxy-3-[(4-methyl-1-piperazinyl)methyl]-1H-indole with acetylcholinesterase inhibitor which is more effective than the acetylcholinesterase inhibitor or 1-[(2-Bromophenyl)sulfonyl]-5-methoxy-3-[(4-methyl-1-piperazinyl)methyl]-1H-indole alone.

In another embodiment, the present invention provides a combination of 1-[(2-Bromophenyl)sulfonyl]-5-methoxy-3-[(4-methyl-1-piperazinyl)methyl]-1H-indole dimesylate monohydrate with acetylcholinesterase inhibitor which is more effective than the acetylcholinesterase inhibitor or 1-[(2-Bromophenyl)sulfonyl]-5-methoxy-3-[(4-methyl-1-piperazinyl)methyl]-1H-indole dimesylate monohydrate alone.

In another embodiment, the present invention provides a combination of pure 5-HT$_6$ receptor antagonist, 1-[(4-Fluorophenyl)sulfonyl]-5-methoxy-3-[(4-methyl-1-piperazinyl)methyl]-1H-indoledihydrochloride and acetylcholinesterase inhibitor.

In another embodiment, the present invention provides a combination of pure 5-HT$_6$ receptor antagonist, 1-[(4-Isopropylphenyl)sulfonyl]-5-methoxy-3-[(4-methyl-1-piperazinyl)methyl]-1H-indole dihydrochloride and acetylcholinesterase inhibitor.

In another embodiment, the present invention relates to the combination wherein the acetylcholinesterase inhibitor is selected from the group consisting of donepezil, galantamine and rivastigmine or a pharmaceutically acceptable salt thereof.

In another embodiment, the present invention relates to the combination wherein the acetylcholinesterase inhibitor is donepezil or a pharmaceutically acceptable salt thereof.

In another embodiment, the present invention relates to the combination wherein the acetylcholinesterase inhibitor is selected from galantamine and rivastigmine or a pharmaceutically acceptable salt thereof.

In another embodiment, the present invention relates to the combination wherein the acetylcholinesterase inhibitor in the combination is donepezil hydrochloride.

In another embodiment, the present invention relates to the combination of 1-[(2-Bromophenyl)sulfonyl]-5-methoxy-3-[(4-methyl-1-piperazinyl)methyl]-1H-indole dimesylate monohydrate with donepezil hydrochloride.

In another embodiment, the present invention relates to the combination of 1-[(2-Bromophenyl)sulfonyl]-5-methoxy-3-[(4-methyl-1-piperazinyl)methyl]-1H-indole dimesylate monohydrate with rivastigmine tartrate.

In another embodiment, the present invention relates to the combination of 1-[(2-Bromophenyl)sulfonyl]-5-methoxy-3-[(4-methyl-1-piperazinyl)methyl]-1H-indole dimesylate monohydrate with galantamine hydrobromide.

In yet another embodiment, the present invention relates to the combination of 1-[(4-Fluorophenyl)sulfonyl]-5-methoxy-3-[(4-methyl-1-piperazinyl)methyl]-1H-indole dihydrochloride with donepezil hydrochloride.

In yet another embodiment, the present invention relates to the combination of 1-[(4-Isopropylphenyl)sulfonyl]-5-methoxy-3-[(4-methyl-1-piperazinyl)methyl]-1H-indole dihydrochloride with donepezil hydrochloride.

In another embodiment the pharmaceutically acceptable salt of the, 1-[(2-Bromophenyl)sulfonyl]-5-methoxy-3-[(4-methyl-1-piperazinyl)methyl]-1H-indole is dihydrochloride salt, dimesylate monohydrate salt, and the like.

In another embodiment the pharmaceutically acceptable salt of pure 5-HT$_6$ receptor antagonist includes but not limited to dimesylate monohydrate salt, dihydrochloride salt, oxalate salt, tartrate salt and the like. Preferably, the pharmaceutically acceptable salt is dimesylate monohydrate salt and dihydrochloride salt. More preferably, the pharmaceutically acceptable salt is dimesylate monohydrate salt.

In another embodiment, the present invention relates to a method of treating Alzheimer's disease comprising administering to a patient in need thereof a therapeutically effective amount of the said combination.

In another embodiment, the present invention relates to a method of treating Alzheimer's disease comprising administering to a patient in need thereof a therapeutically effective amount of 1-[(2-Bromophenyl)sulfonyl]-5-methoxy-3-[(4-methyl-1-piperazinyl)methyl]-1H-indole or a pharmaceutically acceptable salt thereof in combination with acetylcholinesterase inhibitor.

In another embodiment, the present invention relates to a method of treating Alzheimer's disease comprising administering to a patient in need thereof a therapeutically effective amount of 1-[(4-Fluorophenyl)sulfonyl]-5-methoxy-3-[(4-methyl-1-piperazinyl)methyl]-1H-indole or a pharmaceutically acceptable salt thereof in combination with acetylcholinesterase inhibitor.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole or a pharmaceutically acceptable salt thereof in combination with acetylcholinesterase inhibitor.

In another embodiment, the present invention relates to a method of treating Alzheimer's disease comprising administering to a patient in need thereof a therapeutically effective amount of 1-[(2-Bromophenyl)sulfonyl]-5-methoxy-3-

[(4-methyl-1-piperazinyl)methyl]-1H-indole dimesylate monohydrate in combination with acetylcholinesterase inhibitor.

In another embodiment, the present invention relates to a method of treating Alzheimer's disease comprising administering to a patient in need thereof a therapeutically effective amount of 1-[(4-Fluorophenyl)sulfonyl]-5-methoxy-3-[(4-methyl-1-piperazinyl)methyl]-1H-indole dihydrochloride in combination with acetylcholinesterase inhibitor.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole dihydrochloride in combination with acetylcholinesterase inhibitor.

In another embodiment, the present invention relates to a method of treating Alzheimer's disease comprising administering to a patient in need thereof a therapeutically effective amount of 1-[(2-Bromophenyl)sulfonyl]-5-methoxy-3-[(4-methyl-1-piperazinyl)methyl]-1H-indole dimesylate monohydrate in combination with donepezil or a pharmaceutically acceptable salt thereof.

In another embodiment, the present invention relates to a method of treating Alzheimer's disease comprising administering to a patient in need thereof a therapeutically effective amount of 1-[(2-Bromophenyl)sulfonyl]-5-methoxy-3-[(4-methyl-1-piperazinyl)methyl]-1H-indole dimesylate monohydrate in combination with donepezil hydrochloride.

In another embodiment, the present invention relates to 1-[(2-Bromophenyl)sulfonyl]-5-methoxy-3-[(4-methyl-1-piperazinyl)methyl]-1H-indole dimesylate monohydrate for use in the treatment of Alzheimer's disease in combination with acetylcholinesterase inhibitor.

In yet another aspect, the present invention relates to 1-[(4-Fluorophenyl)sulfonyl]-5-methoxy-3-[(4-methyl-1-piperazinyl)methyl]-1H-indole or a pharmaceutically acceptable salt thereof for use in the adjunct treatment of cognitive disorder such as Alzheimer's disease in a patient on treatment with a acetylcholinesterase inhibitor.

In yet another aspect, the present invention relates to the compound, 1-[(4-Isopropylphenyl)sulfonyl]-5-methoxy-3-[(4-methyl-1-piperazinyl)methyl]-1H-indole or a pharmaceutically acceptable salt thereof for use in the adjunct treatment of cognitive disorder such as Alzheimer's disease in a patient on treatment with acetylcholinesterase inhibitor.

In another embodiment, the present invention relates to 1-[(2-Bromophenyl)sulfonyl]-5-methoxy-3-[(4-methyl-1-piperazinyl)methyl]-1H-indole dimesylate monohydrate for use in the treatment of Alzheimer's disease in combination with donepezil or pharmaceutically acceptable salt thereof.

In another embodiment, the present invention relates to 1-[(2-Bromophenyl)sulfonyl]-5-methoxy-3-[(4-methyl-1-piperazinyl)methyl]-1H-indole dimesylate monohydrate for use in the treatment of Alzheimer's disease in combination with donepezil hydrochloride.

In another embodiment, the present invention relates to use of the 1-[(2-Bromophenyl)sulfonyl]-5-methoxy-3-[(4-methyl-1-piperazinyl)methyl]-1H-indole or a pharmaceutically acceptable salt in the manufacture of a medicament for treatment of Alzheimer's disease in combination with acetylcholinesterase inhibitor.

In another embodiment, the present invention relates to use of the 1-[(2-Bromophenyl)sulfonyl]-5-methoxy-3-[(4-methyl-1-piperazinyl)methyl]-1H-indole or a pharmaceutically acceptable salt thereof in the manufacture of a medicament for treatment of Alzheimer's disease in combination with donepezil or a pharmaceutically acceptable salt thereof.

In another embodiment, the present invention relates to use of the 1-[(2-Bromophenyl)sulfonyl]-5-methoxy-3-[(4-methyl-1-piperazinyl)methyl]-1H-indole or a pharmaceutically acceptable salt thereof in the manufacture of a medicament for treatment of Alzheimer's disease in combination with donepezil hydrochloride.

In another embodiment, the present invention relates to use of the 1-[(2-Bromophenyl)sulfonyl]-5-methoxy-3-[(4-methyl-1-piperazinyl)methyl]-1H-indole dimesylate monohydrate in the manufacture of a medicament for treatment of Alzheimer's disease in combination with acetylcholinesterase inhibitor.

In another embodiment, the present invention relates to use of the 1-[(2-Bromophenyl)sulfonyl]-5-methoxy-3-[(4-methyl-1-piperazinyl)methyl]-1H-indole dimesylate monohydrate in the manufacture of a medicament for treatment of Alzheimer's disease in combination with donepezil or a pharmaceutically acceptable salt thereof.

In another embodiment, the present invention relates to use of the 1-[(2-Bromophenyl)sulfonyl]-5-methoxy-3-[(4-methyl-1-piperazinyl)methyl]-1H-indole dimesylate monohydrate in the manufacture of a medicament for treatment of Alzheimer's disease in combination with donepezil hydrochloride.

In another embodiment, the present invention relates to the combination for treatment of Alzheimer's disease, wherein the Alzheimer's disease is mild Alzheimer's disease.

In another embodiment, the present invention relates to the combination for treatment of Alzheimer's disease, wherein the Alzheimer's disease is moderate Alzheimer's disease.

In another embodiment, the present invention relates to the combination for treatment of Alzheimer's disease, wherein the Alzheimer's disease is severe Alzheimer's disease.

In another embodiment, the present invention relates to the combination wherein the active ingredients can be administered to a patient concurrently or separately.

In yet another aspect, the active ingredients of the combination of the present invention are normally administered by formulating the active ingredients into a pharmaceutical composition in accordance with standard pharmaceutical practice.

In yet another aspect, the active ingredients of the combination of the present invention can be administered in all possible routes of administration.

In yet another aspect, the active ingredients of the combination of the present invention may be administered by oral, nasal, local, dermal or parenteral routes.

In yet another aspect, the active ingredients of the combination of the present invention can be administered by the same or different route of administration. For instance, the 5-HT$_6$ receptor antagonist of the instant invention can be administered orally and the acetylcholinesterase inhibitor can be administered transdermally.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, co-solvents, preservatives, wetting agents, thickening agents, antifoaming agents, sweetening agents, flavouring agents, antioxidants, colorants, solubulizers, plasticizer, dispersing agents and the like. Excipients are selected from microcrystalline cellulose, mannitol, lactose, pre-gelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, semi-solids, liquids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

In yet another aspect, the pharmaceutical composition of the combination of the instant invention can be conventional formulations such as immediate release formulations, modified release formulations such as sustained release formulations, delayed release formulations and extended release formulations or new delivery systems such as orally disintegrating formulations and transdermal patches.

The dose of the active compounds can vary depending on factors such as age and weight of patient, nature, route of administration and severity of the disease to be treated and such other factors. Therefore, any reference regarding pharmacologically effective amount of the compounds 1, 2 and 3 refers to the aforementioned factors.

In yet another aspect, the 5-HT$_6$ receptor antagonist can be co-administered with acetylcholinesterase inhibitor at a daily dose of 1 mg to 300 mg; such as 1, 5, 10, 20, 25, 30, 50, 75, 100, 150, 200 or 300 mg, preferably at a daily dose of 10, 25, 30, 50, 75, 100 or 150 mg and most preferably at a daily dose of 10, 25, 50, 75, 100 or 125 mg.

In yet another aspect, the acetylcholinesterase inhibitor can be co-administered with 5-HT$_6$ receptor antagonist at a daily dose of 1 mg to 30 mg; 1, 1.5, 2, 3, 4, 4.5, 5, 6, 8, 9.5, 10, 12, 13, 13.3, 15, 16, 23, 24, 25 or 30 mg, preferably at a daily dose of 1, 1.5, 2, 3, 4, 4.5, 5, 6, 8, 9.5, 10, 12, 13, 13.3, 16, 23, 24, or 25 mg and most preferably at a daily dose of 1.5, 3, 4, 4.5, 5, 6, 8, 9.5, 10, 12, 13.3, 16, 23 or 24 mg.

In yet another aspect, the acetylcholinesterase inhibitor, donepezil can be co-administered with 5-HT$_6$ receptor antagonist at a daily dose of 2 mg to 30 mg; such as 2, 5, 10, 15, 23, 25 or 30 mg, preferably at a daily dose of 2, 5, 10, 23 or 25 mg and most preferably at a daily dose of 5, 10 or 23 mg.

In yet another aspect, the acetylcholinesterase inhibitor, rivastigmine can be co-administered with 5-HT$_6$ receptor antagonist and NMDA receptor antagonist at a daily dose of 0.5 mg to 15 mg; such as 1, 1.5, 3, 4.5, 5, 6, 9.5, 10 or 13.3 mg, preferably at a daily dose of 1, 1.5, 3, 4.5, 5, 6, 9.5 or 13.3 mg and most preferably at a daily dose of 1.5, 3, 4.5, 6, 9.5 and 13.3 mg.

In yet another aspect, the acetylcholinesterase inhibitor, galantamine can be co-administered with 5-HT$_6$ receptor antagonist at a daily dose of 1 mg to 30 mg; such as 1, 2, 4, 6, 8, 12, 16, 24 and 30 mg, preferably at a daily dose of 2, 4, 6, 8, 12, 16 and 24 mg and most preferably at a daily dose of 4, 8, 12, 16 and 24 mg.

In yet another aspect, the treatment comprises administering to the patient 1 mg to 200 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 1 mg to 10 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 25 mg to 125 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 150 mg to 200 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 10 mg to 100 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 10 mg to 50 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 25 mg to 50 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 75 mg to 100 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 1 mg to 25 mg of donepezil or a pharmaceutically acceptable salt thereof, per day.

In yet another aspect, the treatment comprises administering to the patient 5 mg to 25 mg of donepezil or a pharmaceutically acceptable salt thereof, per day.

In yet another aspect, the treatment comprises administering to the patient 5 mg, 10 mg or 23 mg of donepezil or a pharmaceutically acceptable salt thereof, per day.

In yet another aspect, the treatment comprises administering the active compounds to the patient one to three times per day, one to three times per week or one to three times per month. Preferably, the treatment comprises administering the compound to a patient once a day, twice a day or thrice a day. More preferably, the treatment comprises administering the compound to a patient once a day.

The examples given below are provided by the way of illustration only and therefore should not be construed to limit the scope of the invention. Abbreviations:
5-HT$_{1A}$: 5-Hydroxytryptamine 1A receptor
5-HT$_{1B}$: 5-Hydroxytryptamine 1B receptor
5-HT$_{1D}$: 5-Hydroxytryptamine 1D receptor
5-HT$_{2A}$: 5-Hydroxytryptamine 2A receptor
5-HT$_{2C}$: 5-Hydroxytryptamine 2C receptor
5-HT$_4$: 5-Hydroxytryptamine 4 receptor
5-HT$_{5A}$: 5-Hydroxytryptamine 5A receptor
5-HT$_6$: 5-Hydroxytryptamine 6 receptor
5-HT$_7$: 5-Hydroxytryptamine 7 receptor
ANOVA: Analysis of variance
AP: Anterior Posterior
aCSF: Cerebrospinal fluid
cAMP: Cyclic adenosine monophosphate
CaCl$_2$.2H$_2$O: Calcium Chloride dihydrate
DV: Dorsal Ventral
EC$_{50}$: Half maximal effective concentration
EDTA: Ethylenediaminetetraacetic acid
EEG: Electroencephalogram
GPCR: G-Protein Coupled Receptor
HCl: Hydrochloric acid
h: Hour (s)
i.p: Intraperitoneal
KCl: Potassium chloride
K$_b$: Binding constant
K$_i$: Inhibitory constant
LC-MS/MS: Liquid chromatography-Mass spectrometry/Mass spectrometry
mg: Milligram
MgCl$_2$: Magnesium chloride
min: Minute (s)
ML: Medial Lateral
mM: Millimolar
NaCl: Sodium chloride
NaH$_2$PO$_4$.2H$_2$O: Sodium dihydrogen phosphate dihydrate
Na$_2$HPO$_4$.7H$_2$O: Sodium monohydrogen phosphate heptahydrate
nmol/L: Nanomoles per litre
nM: Nanomolar
NPO: Nucleus Pontis Oralis
p.o.: Per oral
S.E.M.: Standard error of the mean
θ: Theta

EXAMPLE 1

Determination of K$_b$ Values at 5-HT$_6$ Receptor:
A stable CHO cell line expressing recombinant human 5-HT$_6$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compound were added along with 10 µM of serotonin in OptiMEM medium to the cells. The incubation was continued at 37° C. in CO$_2$ incubator for 4 hours. Medium was removed and cells were washed with phosphate buffered saline. The cells were lysed and luciferase activity was measured in a Luminometer. Luminescence units were plotted against the compound concentrations using Graphpad software. EC$_{50}$ values of the compounds were defined as the concentration required in reducing the luciferase activity by 50%. The K$_b$ values were calculated by feeding the concentration of agonist used in the assay and its EC$_{50}$ value in the same software.

References: *Molecular Brain Research*, 2001, 90, 110-117 and *British Journal of Pharmacology*, 2006, 148, 1133-1143.

Compounds 1, 2 and 3 exhibit antagonistic activity in CRE-Luc based reporter gene assay on human recombinant 5-HT$_6$ receptor with no detectable agonist activity. The K$_b$ values tabulated below are average of three independent experiments.

| S. No | Example | K$_b$ (nM) |
|---|---|---|
| 1 | Compound 1 | 4.2 ± 0.9 |
| 2 | Compound 2 | 7.2 ± 1.8 |
| 3 | Compound 3 | 1.6 ± 0.3 |

EXAMPLE 2

Determination of K$_i$ Value at 5-HT$_6$ Receptor
Compound was tested at MDS pharma services and Novascreen according to the following procedures.
Materials and Methods:
Receptor source: Human recombinant expressed in Hela cells
Radioligand: [$^3$H]-LSD (60-80 Ci/mmol)
Final ligand concentration—[1.5 nM]
Non-Specific Ligand: 5 µM Serotonin (5-HT)
Reference compound: Methiothepin mesylate
Positive control: Methiothepin mesylate
Incubation conditions: Reactions were carried out in 50 mM Tris-HCl (pH 7.4) containing 10 mM MgCl$_2$, 0.5 mM EDTA for 60 minutes at 37° C. The reaction was terminated by rapid vacuum filtration onto the glass fiber filters. Radioactivity trapped onto the filters was determined and compared to the control values in order to ascertain any interactions of the test compound(s) with the cloned serotonin 5-HT$_6$ binding site.
Reference: *Molecular Pharmacology*, 1993, 43, 320-327.
Compounds 1, 2 and 3 selectively bind to 5-HT$_6$ receptor when tested by the in-vitro radioligand binding technique on human recombinant 5-HT$_6$ receptor. The K$_i$ values are tabulated below.

| S. No | Example | K$_i$ (nM) |
|---|---|---|
| 1 | Compound 1 | 2.04 |
| 2 | Compound 2 | 4.96 |
| 3 | Compound 3 | 3.67 |

EXAMPLE 3

Determination of K$_i$ Value at 5-HT$_{2A}$ Receptor
Compound was tested according to the following procedures.
Materials and Methods:
Receptor source: Recombinant mammalian cells
Radioligand: [$^3$H]-Ketanserine (47.3 Ci/mmol)
Final ligand concentration—[1.75 nM]
Non-Specific Ligand: 0.1 mM 1-Naphthylpiperazine (1-NP)

Reference compound: 1-Naphthylpiperazine (1-NP)
Positive control: 1-Naphthylpiperazine (1-NP)
Incubation conditions: Reactions were carried out in 67 mM Tris-HCl (pH 7.4) for 1 hour at 37° C. The reaction was terminated by rapid vacuum filtration onto the glass fiber filters. Radioactivity trapped onto the filters was determined and compared to the control values in order to ascertain any interactions of the test compound(s) with the cloned serotonin $5\text{-}HT_{2A}$ binding site.
Reference: *Methods in Molecular Biology*, 2002, 190, 31-49
Compounds 1, 2 and 3 bind weakly to $5\text{-}HT_{2A}$ receptor when tested by the in-vitro radioligand binding technique on human recombinant $5\text{-}HT_{2A}$ receptor. The $K_i$ values tabulated below are average of three independent experiments.

| S. No | Example | $K_i$ |
|---|---|---|
| 1 | Compound 1 | 2514 ± 377 nM |
| 2 | Compound 2 | >10 µM |
| 3 | Compound 3 | 926 ± 317 nM |

EXAMPLE 4

Test compounds were also evaluated for their $5\text{-}HT_6$ receptor selectivity over closely related serotonin subtypes like $5\text{-}HT_{1A}$, $5\text{-}HT_{1B}$, $5\text{-}HT_{1D}$, $5\text{-}HT_{2A}$, $5\text{-}HT_{2C}$, $5\text{-}HT_4$, $5\text{-}HT_{5A}$ and $5\text{-}HT_7$ in commercial panel at Novascreen. Compounds 1, 2 and 3 have shown selectivity of more than 250-fold over these receptor subtypes.

EXAMPLE 5

Object Recognition Task Model
The cognition enhancing properties of compounds of this invention were estimated using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) in the absence of any objects on day 1.

Rats received vehicle or test compounds or cholinesterase inhibitors or test compound and cholinesterase inhibitors, before familiar ($T_1$) and choice ($T_2$) trials. During the familiarization phase ($T_1$), the rats were placed individually in the arena for 3 minutes, in which two identical objects ($a_1$ and $a_2$) were positioned 10 cm from the wall. 24 hours after $T_1$, trial for long-term memory test was assessed. The same rats were placed in the same arena as they were placed during $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects (a1+a2).
$T_2$ is the total time spent exploring the familiar object and novel object (a3+b).

Figure 1B:
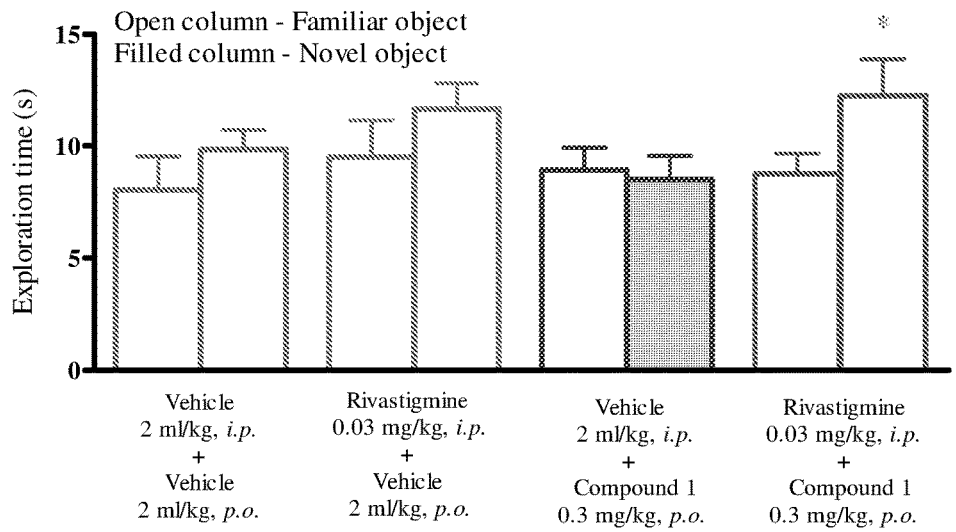
Figure 1C:
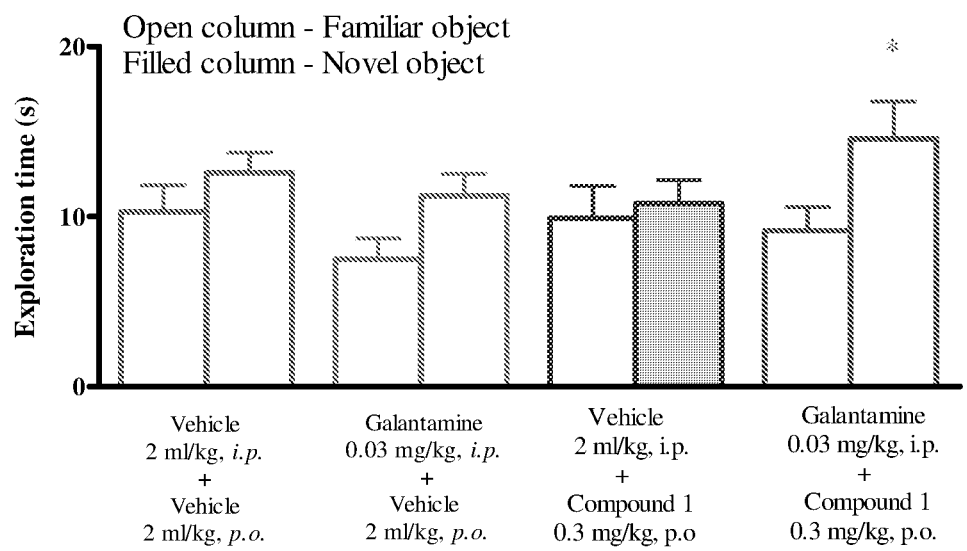

The vehicle treated group did not show significant preference for the novel object, indicating lack of memory for the familiar object. Similarly, neither cholinesterase inhibitors nor the test compounds alone treated groups showed no preference for the novel object, again indicating lack of memory for the familiar object. However, the group treated with a combination of both cholinesterase inhibitors and test compounds showed preference for the novel object indicating significant improvement in memory. The results of this study are provided in FIGS. 1a to 1c.

The object recognition test was performed as described in *Behavioural Brain Research*, 1988, 31, 47-59.

EXAMPLE 6

Evaluation of Test Compound on Acetylcholine Modulation in Ventral Hippocampus of Male Wistar Rats
Experimental Procedure Male Wistar rats (240-300 g body weight) were stereotaxically implanted with a microdialysis guide cannula in ventral hippocampus (AP: −5.2 mm, ML: +5.0 mm, DV: −3.8 mm) under isoflurane anesthesia. Co-ordinates were taken according to atlas for the rat brain (Paxinos and Watson 2004) with reference points taken from bregma and vertical from the skull. The rats were allowed to recover individually for four-five days in a round bottom Plexiglas bowl with free access to feed and water.

One day prior to the microdialysis experiment, rats were connected to a dual quartz lined two-channel liquid swivel (Instech, UK) on a counter balance lever arm, which allowed unrestricted movements of the animal. Sixteen hours before start of study, a pre-equilibrated microdialysis probe (4 mm dialysis membrane) was inserted into the ventral hippocampus through the guide cannula and perfused overnight with artificial cerebrospinal fluid (aCSF; NaCl 147 mM, KCl 3 mM, $MgCl_2$ 1 mM, $CaCl_2 \cdot 2H_2O$ 1.3 mM, $NaH_2PO_4 \cdot 2H_2O$ 0.2 mM and $Na_2HPO_4 \cdot 7H_2O$ 1 mM, pH 7.2) containing 0.3 µM neostigmine bromide at a flow rate of 0.2 µL/min. On the day of experiment, perfusion rate was changed to 1.2 µL/min and stabilization period of atleast 2 hours was maintained. After stabilization period, five basal samples were collected at 20 min intervals prior to the administration of compound 1 (1 or 3 mg/kg, p.o.). Dialysate samples were collected for additional period of 6 h using CMA/170 refrigerated fraction collector.

Acetylcholine in dialysate was quantified in the calibration range of 1.36 nmol to 547.7 nmol/L using LC-MS/MS method.

All microdialysis data were plotted as percent change from mean dialysate basal concentrations with 100% defined as the average of five predose values. The AUC was calculated by trapezoidal rule using WinNonlin® (5.0.1 version, Pharsight Corp. CA). The statistical significance between the mean AUC values of treatment group with vehicle was calculated using Dunnett's multiple comparison test. For each treatment group, the percent increase in acetylcholine levels was compared to the vehicle group using two-way analysis of variance (time and treatment), followed by Bonferroni post test. Statistical significance was considered at a p value less than 0.05. Incorrect probe placement was considered as criteria to reject the data from animal.

Results:
Compound 1 produced about 172% increase in hippocampal acetylcholine levels at the tested dose of 3 mg/kg, p.o.

Figure 2:
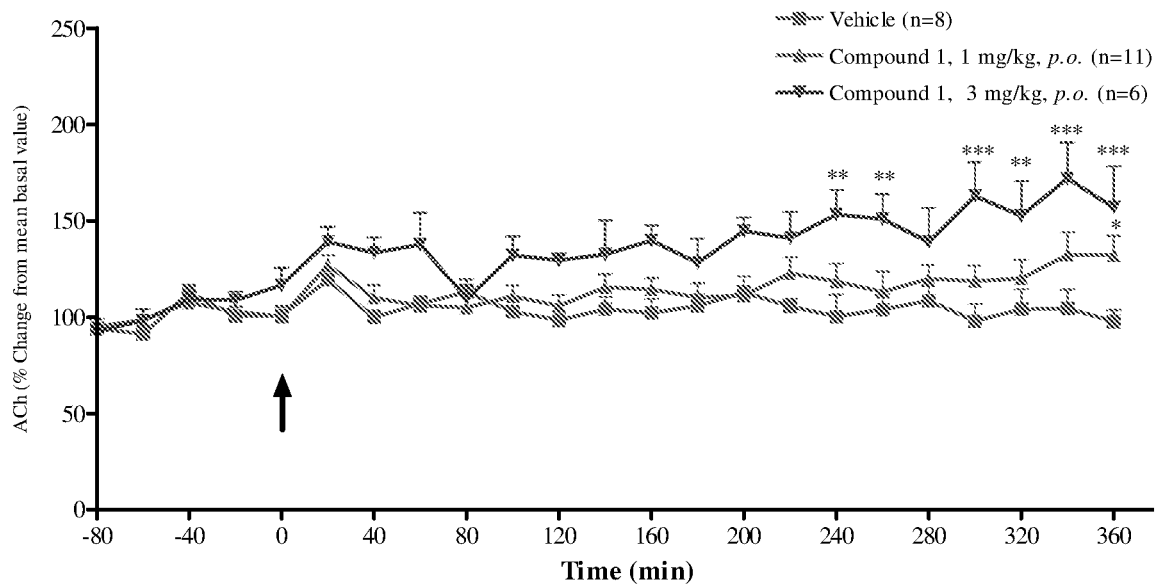
FIG. 2 illustrates the effect of compound 1 on acetylcholine levels in ventral hippocampus of male Wistar rats.
Figure 2:
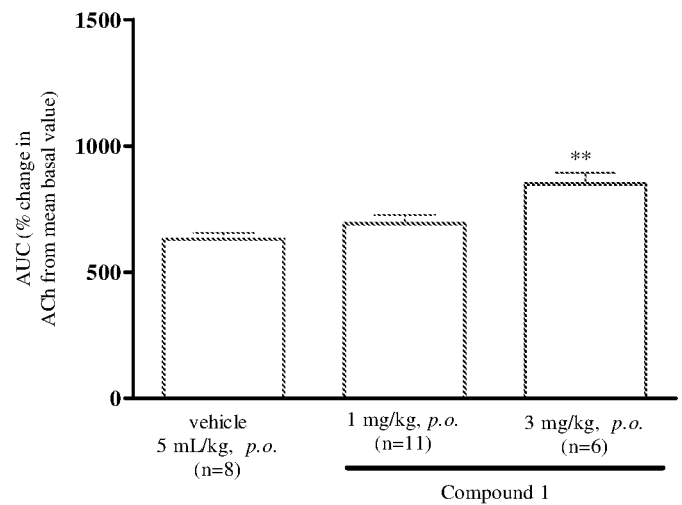

Area under the curve value calculated to assess the overall effect of compound 1 was significantly higher than the vehicle treatment (FIG. 2).

Reference: Paxinos G and Watson C (2004) Rat brain in stereotaxic coordinates. Academic Press, New York

EXAMPLE 7

Evaluation of Combination Treatment on Acetylcholine Modulation in Ventral Hippocampus of Male Wistar Rats Experimental Procedure:

Procedure for the stereotaxic surgery was similar as described in Example 6. However, there were minor modifications in the microdialysis experiment.

After surgical recovery of 4-5 days, male Wistar rats were connected to dual quartz lined two-channel liquid swivel (Instech, UK) on a counter balance lever arm, which allowed unrestricted movements of the animal. Sixteen hours before start of study, a pre-equilibrated microdialysis probe (4 mm dialysis membrane) was inserted into the ventral hippocampus through the guide cannula. On the day of study, the probe was perfused with aCSF at a flow rate of 1.5 µL/min and a stabilization period of 2 h was maintained. Five basal samples were collected at 20 min intervals prior to the treatment of compound 1 (3 mg/kg, p.o.) or vehicle. Donepezil (1 mg/kg, s.c.) or rivastigmine (0.5 mg/kg, s.c.) was administered 30 min after administration of compound 1. Dialysate samples were collected for an additional period of 4 hours post treatment of compound 1. Dialysates were stored below −50° C. prior to analysis.

Acetylcholine in dialysate was quantified using LC-MS/MS method in the calibration range of 0.103 to 103.491 nmol/L.

All microdialysis data for acetylcholine was plotted as percent change from mean dialysate basal concentrations with 100% defined as the average of five pre-dose values. The percent change in acetylcholine levels after combination treatment were compared with donepezil using two-way analysis of variance (time and treatment), followed by Bonferroni's posttest. Area under the curve (AUC) values for percent change in acetylcholine levels were calculated and the statistical significance between the mean AUC value after combination treatment was compared against AUC values after donepezil treatment using one-way ANOVA followed by Dunnett's test. Statistical significance was considered at a p value less than 0.05. Incorrect probe placement was considered as criteria to reject the data from animal.

Results:

Treatment with donepezil (1 mg/kg, s.c.) produced significant increase in hippocampal acetylcholine levels and reached to the maximum of 703±134% of basal levels. Compound 1 in combination with donepezil (1 mg/kg, s.c.) produced significant increase in acetylcholine levels and peak levels reached up to 1363±242% of pre-dose levels after 3 mg/kg, p.o., (FIG. 3).

Treatment with rivastigmine (0.5 mg/kg, s.c.) produced about 3 fold increase in hippocampal acetylcholine level. Compound 1 in combination with rivastigmine (0.5 mg/kg, s.c.) produced significant increase in acetylcholine levels and peak levels reached up to 747±54% of pre-dose levels after 3 mg/kg, p.o. (FIG. 4).

Figure 3:
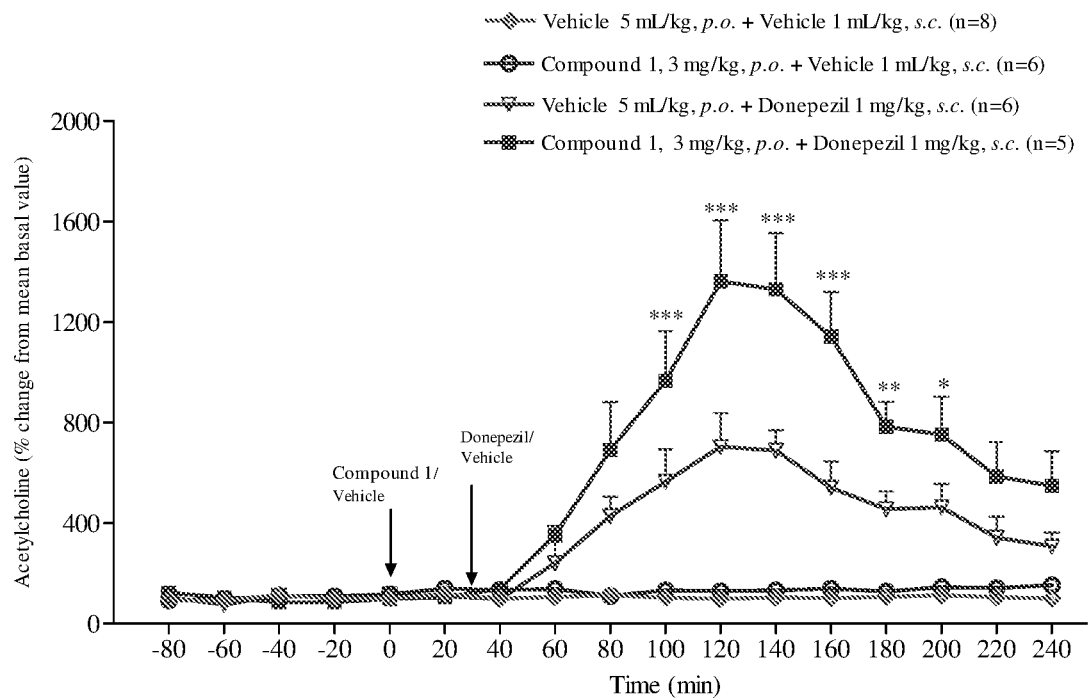
FIG. 3 illustrates the effect of compound 1 alone and in combination with donepezil on extracellular levels of acetylcholine in ventral hippocampus of male Wistar rats.
Figure 3:
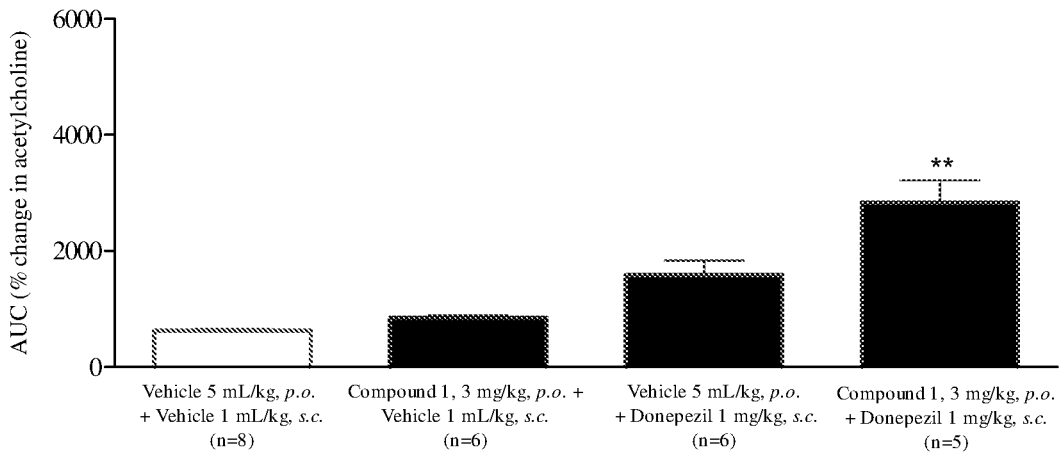
Figure 4:
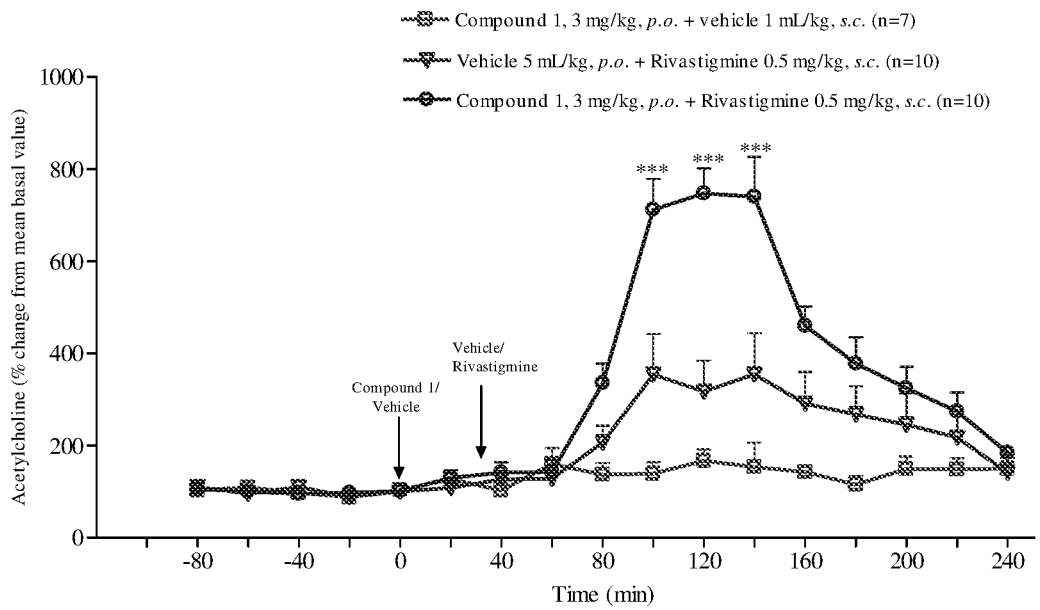
FIG. 4 illustrates the effect of compound 1 alone and in combination with rivastigmine on extracellular levels of acetylcholine in ventral hippocampus of male Wistar rats.
Figure 4:
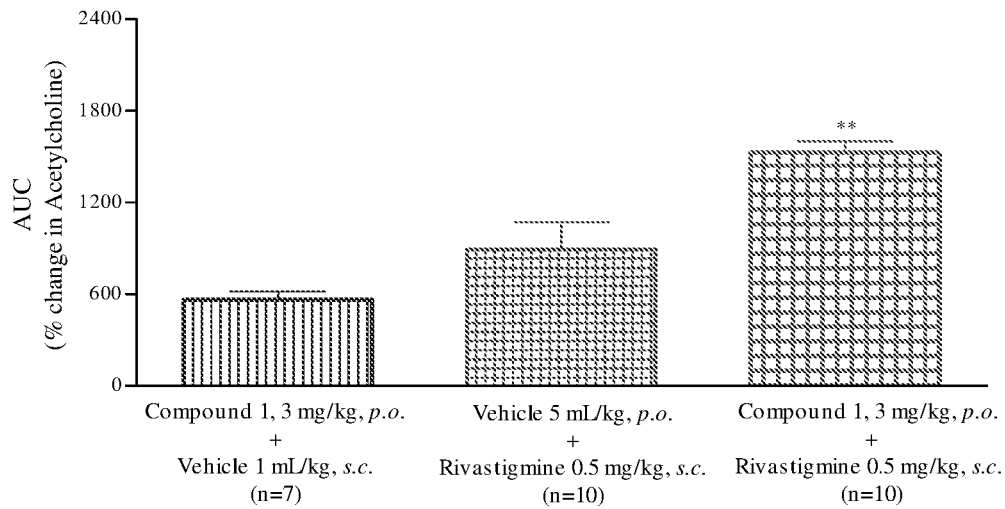

Mean area under the curve values (AUC) calculated after combination treatment of compound 1 (3 mg/kg, p.o.) and donepezil, and compound 1 (3 mg/kg, p.o.) and rivastigmine were significantly higher compared to donepezil (1 mg/kg, s.c.) and rivastigmine (0.5 mg/kg, s.c.) alone respectively (FIGS. 3 and 4).

Reference: Paxinos G. and Watson C. (2004) Rat brain in stereotaxic coordinates. Academic Press, New York

EXAMPLE 8

Evaluation of Theta Modulation in Dorsal Hippocampus of Anesthetized Male Wistar Rats Synchronous hippocampal EEG activity occurring in a θ rhythm (frequency range of 4 to 8 Hz) has been associated with mnemonic processes in vivo. Experimental Procedure:

Male Wistar rats (240-320 g) were anesthetized with 1.2 to 1.5 g/kg urethane intraperitoneally, under anesthesia a catheter was surgically implanted in the left femoral vein for administration of drugs. After cannulation, the animal was placed in a stereotaxic frame for implanting an electrode (stainless steel wire, Plastics One) into the dorsal hippocampus (AP, −3.8 mm; ML, +2.2 mm; DV, −1.5 mm; Paxinos and Watson, 1994) and bipolar stimulating electrode (untwisted stainless steel wires, separated by 0.75-1.0 mm at their tips, Plastics One) was implanted in the Nucleus Pontis Oralis (NPO; AP, −7.8 mm; ML, ±1.8 mm; DV, −6.0 mm; Paxinos and Watson, 1994). Additionally one electrode was implanted into the cerebellum which served as a reference. Hippocampal θ rhythm was evoked via a 6-s electrical stimulation train (20-160 µA, 0.3-ms pulse duration, 250 Hz) delivered to the NPO at a rate of 0.01 trains/s with a Grass S88 stimulator and PSIU6 stimulus isolation unit (Grass Medical Instruments, Quincy, Mass.). EEG was recorded at a rate of 1000 Hz using Ponemah (Version 5.2) software and stored for off-line analysis using NeuroScore™ (Version 3.0). Baseline amplitude level was achieved by using the current required to elicit θ rhythm to 50% of the maximal amplitude under control conditions. After the stabilization period of 1 h, baseline recording was done for 30 min followed by the treatment of vehicle or compound 1 (1 mg/kg, i.v.). Donepezil (0.3 mg/kg, i.v.) was administered 30 min after compound 1 treatment and recording was continued for additional 1 h.

Power in the θ rhythm frequency in the stimulation period during the 30 min baseline period was calculated and the percent changes in these measures post treatment were calculated. The percent change in relative theta power after combination treatment was compared with donepezil using two-way analysis of variance (time and treatment), followed by Bonferroni's posttest. Statistical significance was considered at a p value less than 0.05.

Figure 5:
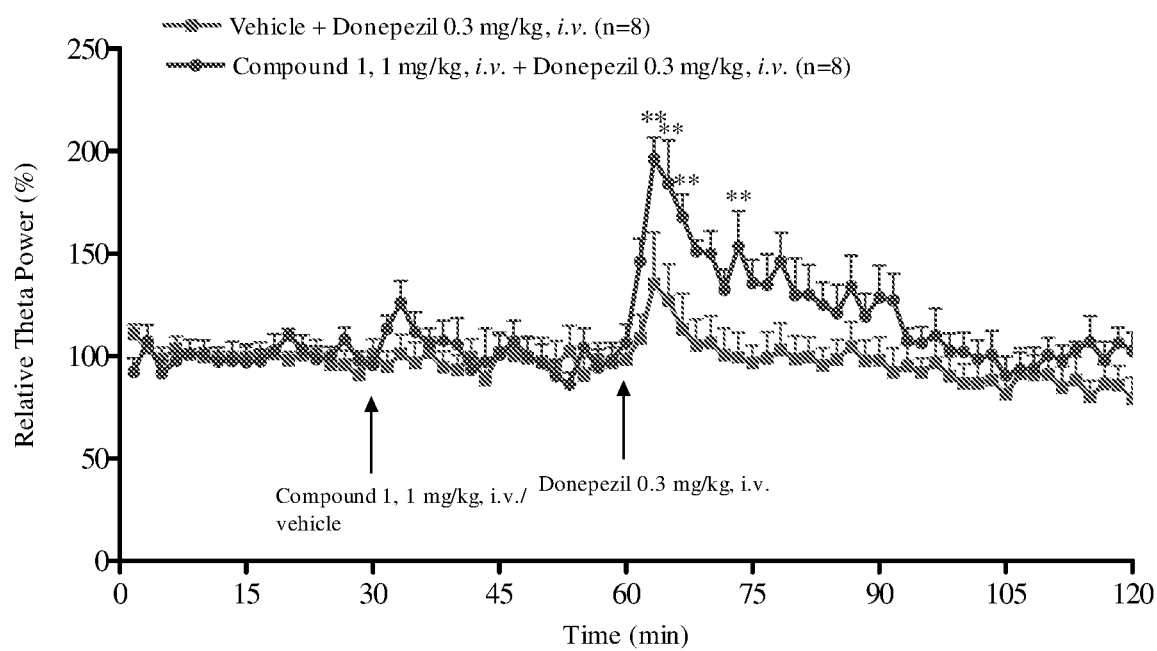
FIG. 5 illustrates the effect of compound 1 and in combination with donepezil on evoked theta modulation in dorsal hippocampus of anesthetized male Wistar rats.

Results:

Treatment with donepezil (0.3 mg/kg, i.v.) produced moderate increase in hippocampal theta power. Compound 1 (1 mg/kg, i.v.) in combination with donepezil (0.3 mg/kg, i.v.) produced significant increase in theta power levels and peak levels reached up to 196±10% of pre-dose levels (FIG. 5).

Reference: Paxinos G. and Watson C. (2004) Rat brain in stereotaxic coordinates. Academic Press, New York.

EXAMPLE 9

Rodent Pharmacokinetic Study for Assessment of Drug Interaction:

Male Wistar rats (260±50 grams) were used as experimental animals. Animals were housed individually in polypropylene cages and acclimatized for three days prior to study. Rats were randomly divided into following groups prior to administration of compound 1 or co-treatment of donepezil and compound 1.

Group 1: compound 1 (3 mg/kg, p.o.)+Vehicle (2 mL/kg, s.c.)
Group 2: Vehicle (5 mL/kg, p.o.)+Donepezil (1 mg/kg, s.c.)
Group 3: compound 1 (3 mg/kg, p.o.)+Donepezil (1 mg/kg, s.c.)

Water was used as a vehicle to dissolve compound 1 and donepezil. Donepezil or vehicle for donepezil was administered subcutaneously 30 minutes after oral administration of compound 1 or vehicle for compound 1.

Blood was collected through retro orbital plexus under isoflurane anesthesia. Collected blood was transferred into a pre-labeled eppendorf tube containing 10 μL of sodium heparin as an anticoagulant. Blood samples were collected at following time points: 0.33, 0.66, 1, 1.5, 2, 4, 6, 8 and 24 hours post dose. Blood was centrifuged at 4000 rpm for 10 minutes. Plasma was separated and stored frozen at −80 °C. until analysis. The concentrations of the compound 1 and donepezil were quantified in plasma by qualified LC-MS/MS method using suitable extraction technique. The test compounds were quantified in the calibration range around 0.05-100 ng/mL in plasma. Study samples were analyzed using calibration samples in the batch and quality control samples spread across the batch.

Pharmacokinetic parameters $C_{max}$, $T_{max}$ and $AUC_{last}$ were calculated by non-compartmental model using Phoenix WinNonlin 6.4.0 version Software package.

| S. No | Group | Analyte | $C_{max}$ (ng/mL) | $t_{max}$ # (hr) | $AUC_{last}$ (ng * hr/mL) |
|---|---|---|---|---|---|
| 1 | Group 1 | Compound 1 | 2.97 ± 1.33 | 0.33 (0.33-0.66) | 6.07 ± 1.78 |
| 2 | Group 2 | Donepezil | 44.6 ± 9.26 | 0.50 (0.50-1.00) | 163 ± 28.4 |
| 3 | Group 3 | Compound 1 | 1.98 ± 1.25 | 0.33 (0.33-0.66) | 4.80 ± 2.08 |
|   |         | Donepezil  | 52.1 ± 8.21 | 1.00 (0.50-1.00) | 187 ± 27.6 |

N=8-10 animal per group, values mean±SD and # Values are represented as median (min-max).

Results:

No significant difference in plasma exposures of compound 1 or donepezil administered either alone or in combination.

What is claimed is:

1. A combination consisting essentially of a pure 5-HT$_6$ receptor antagonist and an acetylcholinesterase inhibitor; wherein:
   the pure 5-HT$_6$ receptor antagonist is selected from,
   1-[(2-Bromophenyl)sulfonyl]-5-methoxy-3-[(4-methyl-1-piperazinyl)methyl]-1H-indole;
   1-[(4-Fluorophenyl)sulfonyl]-5-methoxy-3-[(4-methyl-1-piperazinyl)methyl]-1H-indole; and
   1-[(4-Isopropylphenyl)sulfonyl]-5-methoxy-3-[(4-methyl-1-piperazinyl)methyl]-1H-indole;
   or a pharmaceutically acceptable salt thereof.

2. The combination as claimed in claim 1, wherein the pure 5-HT$_6$ receptor antagonist is, 1-[(2-Bromophenyl)sulfonyl]-5-methoxy-3-[(4-methyl -1-piperazinyl)methyl]-1H-indole or a pharmaceutically acceptable salt thereof.

3. The combination as claimed in claim 1, wherein the pharmaceutically acceptable salt of the pure 5-HT$_6$ receptor antagonist is,
   1-[(2-Bromophenyl)sulfonyl]-5-methoxy-3-[(4-methyl-1-piperazinyl)methyl]-1H-indole dimesylate monohydrate;
   1-[(4-Fluorophenyl)sulfonyl]-5-methoxy-3-[(4-methyl-1-piperazinyl)methyl]-1H-indole dihydrochloride; or
   1-[(4-Isopropylphenyl)sulfonyl]-5-methoxy-3-[(4-methyl-1-piperazinyl)methyl]-1H-indole dihydrochloride.

4. The combination as claimed in claim 1, wherein the acetylcholinesterase inhibitor is donepezil, galantamine or rivastigmine or a pharmaceutically acceptable salt thereof.

5. The combination as claimed in claim 4, wherein the acetylcholinesterase inhibitor is donepezil or rivastigmine or a pharmaceutically acceptable salt thereof.

6. The combination as claimed in claim 5, wherein the acetylcholinesterase inhibitor is donepezil hydrochloride.

7. The combination as claimed in claim 1, for the treatment of cognitive disorders in a patient.

8. The combination as claimed in claim 7, wherein the cognitive disorder is selected from Alzheimer's disease, schizophrenia, Parkinson's disease, lewy body dementia, vascular dementia and frontotemporal dementia.

9. A method of treatment of cognitive disorder comprising administering to a patient in need thereof, a therapeutically effective amount of the combination as claimed in claim 1.

10. The method of treatment as claimed in claim 9, wherein the cognitive disorder is selected from Alzheimer's disease, schizophrenia, Parkinson's disease, lewy body dementia, vascular dementia and frontotemporal dementia.

11. A method of treating Alzheimer's disease in a patient comprising administering to said patient a therapeutically effective amount of 1-[(2-Bromophenyl)sulfonyl]-5-methoxy-3-[(4-methyl-1-piperazinyl)methyl]-1H-indole or a pharmaceutically acceptable salt thereof and acetylcholinesterase inhibitor.

12. A method of treating Alzheimer's disease in a patient on stable treatment with acetylcholinesterase inhibitor comprising administering to said patient a therapeutically effective amount of 1-[(2-Bromophenyl)sulfonyl]-5-methoxy-3-[(4-methyl-1-piperazinyl)methyl]-1H-indole or a pharmaceutically acceptable salt thereof.

13. The method as claimed in claim 11, wherein the pharmaceutically acceptable salt of 1-[(2-Bromophenyl)sulfonyl]-5-methoxy-3-[(4-methyl-1-piperazinyl)methyl]-1H-indole is 1-[(2-Bromophenyl)sulfonyl]-5-methoxy-3-[(4-methyl-1-piperazinyl)methyl]-1H-indole dimesylate monohydrate.

14. The method as claimed in claim 11, wherein the acetylcholinesterase inhibitor is donepezil and rivastigmine or a pharmaceutically acceptable salt thereof.

15. The method of treating Alzheimer's disease as claimed in claim 11, wherein the patient is administered 1 mg to 200 mg of 1-[(2-Bromophenyl)sulfonyl]-5-methoxy-3-[(4-methyl-1-piperazinyl)methyl]-1H-indole or a pharmaceutically acceptable salt thereof per day.

16. The method of treating Alzheimer's disease as claimed in claim 11, wherein the patient is administered 1 mg to 10 mg of 1-[(2-Bromophenyl)sulfonyl]-5-methoxy-3-[(4-methyl-1-piperazinyl)methyl]-1H-indole or a pharmaceutically acceptable salt thereof per day.

17. The method of treating Alzheimer's disease as claimed in claim 11, wherein the patient is administered 25 mg to 125 mg of 1-[(2-Bromophenyl)sulfonyl]-5-methoxy-3-[(4-methyl-1-piperazinyl)methyl]-1H-indole or a pharmaceutically acceptable salt thereof per day.

18. The method of treating Alzheimer's disease as claimed in claim 11, wherein the patient is administered 150 mg to 200 mg of 1-[(2-Bromophenyl)sulfonyl]-5-methoxy-3-[(4-methyl-1-piperazinyl)methyl]-1H-indole or a pharmaceutically acceptable salt thereof per day.

19. The method of treating Alzheimer's disease as claimed in claim 11, wherein the patient is administered 25 mg to 75 mg of 1-[(2-Bromophenyl)sulfonyl]-5-methoxy-3-[(4-methyl-1-piperazinyl)methyl]-1H-indole or pharmaceutically acceptable salt thereof per day.

20. The method of treating Alzheimer's disease as claimed in claim 11, wherein the patient is administered 75 mg to 150 mg of 1-[(2-Bromophenyl)sulfonyl]-5-methoxy-3-[(4-methyl-1-piperazinyl)methyl]-1H-indole or a pharmaceutically acceptable salt thereof per day.

21. The method of treating Alzheimer's disease as claimed in claim 11, wherein the patient is administered 1 mg to 30 mg of donepezil or a pharmaceutically acceptable salt thereof per day.

22. The method of treating Alzheimer's disease as claimed in claim 11, wherein the patient is administered 5 mg to 25 mg of donepezil or a pharmaceutically acceptable salt thereof per day.

23. The method of treating Alzheimer's disease as claimed in claim 11, wherein the patient is administered 10 mg to 25 mg of donepezil or a pharmaceutically acceptable salt thereof per day.

24. A pharmaceutical composition comprising the combination as claimed in claim 1, and pharmaceutically acceptable excipients or combination thereof.

25. The pharmaceutical composition as claimed in claim 24, for the treatment of cognitive disorders selected from Alzheimer's disease, schizophrenia, Parkinson's disease, lewy body dementia, vascular dementia and frontotemporal dementia.

26. The pharmaceutical composition as claimed in claim 24, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 1 mg to 300 mg.

27. The pharmaceutical composition as claimed in claim 24, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 35 mg to 200 mg.

28. The pharmaceutical composition as claimed in claim 24, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 200 mg to 300 mg.

29. The pharmaceutical composition as claimed in claim 24, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 75 mg or 150 mg.

30. The pharmaceutical composition as claimed in claim 24, wherein the donepezil or a pharmaceutically acceptable salt thereof is present in an amount of 2 mg to 30 mg.

31. The pharmaceutical composition as claimed in claim 24, wherein the donepezil or a pharmaceutically acceptable salt thereof is present in an amount of 5 mg to 25 mg.

32. The pharmaceutical composition as claimed in claim 24, wherein the donepezil or a pharmaceutically acceptable salt thereof is present in an amount of 5 mg.

33. The pharmaceutical composition as claimed in claim 24, wherein the donepezil or a pharmaceutically acceptable salt thereof is present in an amount of 10 mg.

34. The pharmaceutical composition as claimed in claim 24, wherein the donepezil or a pharmaceutically acceptable salt thereof is present in an amount of 23 mg.

35. The method of treating Alzheimer's disease as claimed in claim 11, wherein the 1-[(2-Bromophenyl)sulfonyl]-5-methoxy-3-[(4-methyl-1-piperazinyl)methyl]-1H-indole or a pharmaceutically acceptable salt thereof is administered to the patient by oral, nasal, local, dermal or parenteral routes.

36. The method of treating Alzheimer's disease as claimed in claim 11, wherein the 1-[(2-Bromophenyl)sulfonyl]-5-methoxy-3-[(4-methyl-1-piperazinyl)methyl]-1H-indole or a pharmaceutically acceptable salt thereof is administered to the patient one to three times per day, one to three times per week or one to three times per month.

37. The method as claimed in claim 12, wherein the pharmaceutically acceptable salt of 1-[(2-Bromophenyl)sulfonyl]-5-methoxy-3-[(4-methyl-1-piperazinyl)methyl]-1H-indole is 1-[(2-Bromophenyl)sulfonyl]-5-methoxy-3-[(4-methyl-1-piperazinyl)methyl]-1H-indole dimesylate monohydrate.

38. The method as claimed in claim 12, wherein the acetylcholinesterase inhibitor is donepezil and rivastigmine or a pharmaceutically acceptable salt thereof.

* * * * *